United States Patent [19]

Morita et al.

[11] 4,148,606
[45] Apr. 10, 1979

[54] STERILIZATION OF DIALYZER

[75] Inventors: Minoru Morita, Yokohama; Yoshishige Fujii, Otsu; Yasuo Taniguchi, Hikone, all of Japan

[73] Assignee: Toray Industries, Inc., Tokyo, Japan

[21] Appl. No.: 835,597

[22] Filed: Sep. 22, 1977

[30] Foreign Application Priority Data

Sep. 24, 1976 [JP] Japan .................... 51-113716

[51] Int. Cl.² .................. A61M 1/03; A61L 1/00; A61L 13/00
[52] U.S. Cl. ................................. 422/21; 422/48
[58] Field of Search .............. 23/258.5 R, 258.5 A, 23/258.5 M, 258.5 MH; 21/54 R, 58

[56] References Cited

U.S. PATENT DOCUMENTS

| | | | |
|---|---|---|---|
| 2,785,313 | 3/1957 | Trump | 21/54 X |
| 2,839,355 | 6/1958 | George | 21/58 |
| 2,904,392 | 9/1959 | Pomerantz et al. | 21/54 R |
| 3,117,832 | 1/1964 | Thomas | 21/58 |
| 3,537,967 | 11/1970 | Kelley et al. | 21/54 R UX |
| 3,618,283 | 11/1971 | Moore et al. | 21/58 X |
| 3,725,003 | 4/1973 | Moore et al. | 21/58 |
| 3,750,367 | 8/1973 | Barker et al. | 21/58 X |
| 3,758,273 | 9/1973 | Johnston et al. | 21/54 R |
| 3,851,436 | 12/1974 | Fraser et al. | 23/258.5 A UX |
| 3,948,601 | 4/1976 | Fraser et al. | 23/258.5 R X |

FOREIGN PATENT DOCUMENTS

| | | | |
|---|---|---|---|
| 942374 | 11/1963 | United Kingdom | 21/54 R |
| 947699 | 1/1974 | United Kingdom | 21/54 R |

OTHER PUBLICATIONS

Morganstern et al., "The Future of Radiation Sterilization", presented 4/25-28/77-2nd J & J. Conf. on Sterilization.

Primary Examiner—Barry S. Richman
Attorney, Agent, or Firm—Miller & Prestia

[57] ABSTRACT

Sterilization of a dialyzer, using a saturated and wet semipermeable membrane and irradiating said dialyzer in the presence of an antibacterial agent. The method is especially effective and safe, affords elimination of labor for preparation for dialysis, and has special utility when the dialyzer is an artificial kidney containing a multiplicity of hollow filament semipermeable membranes.

19 Claims, 3 Drawing Figures

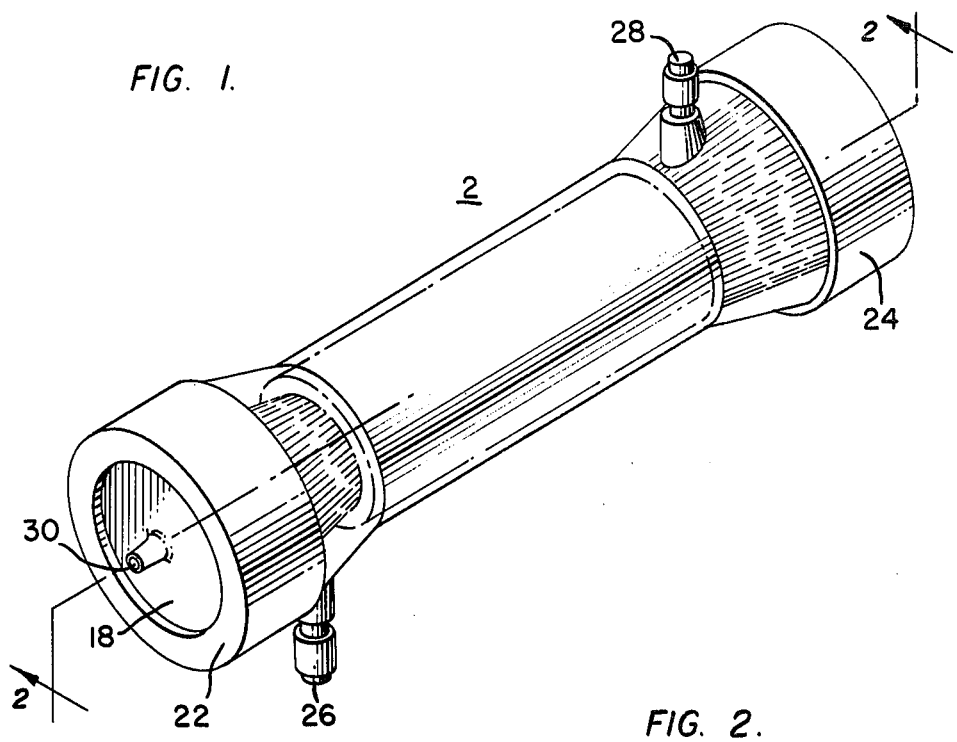
FIG. 1.
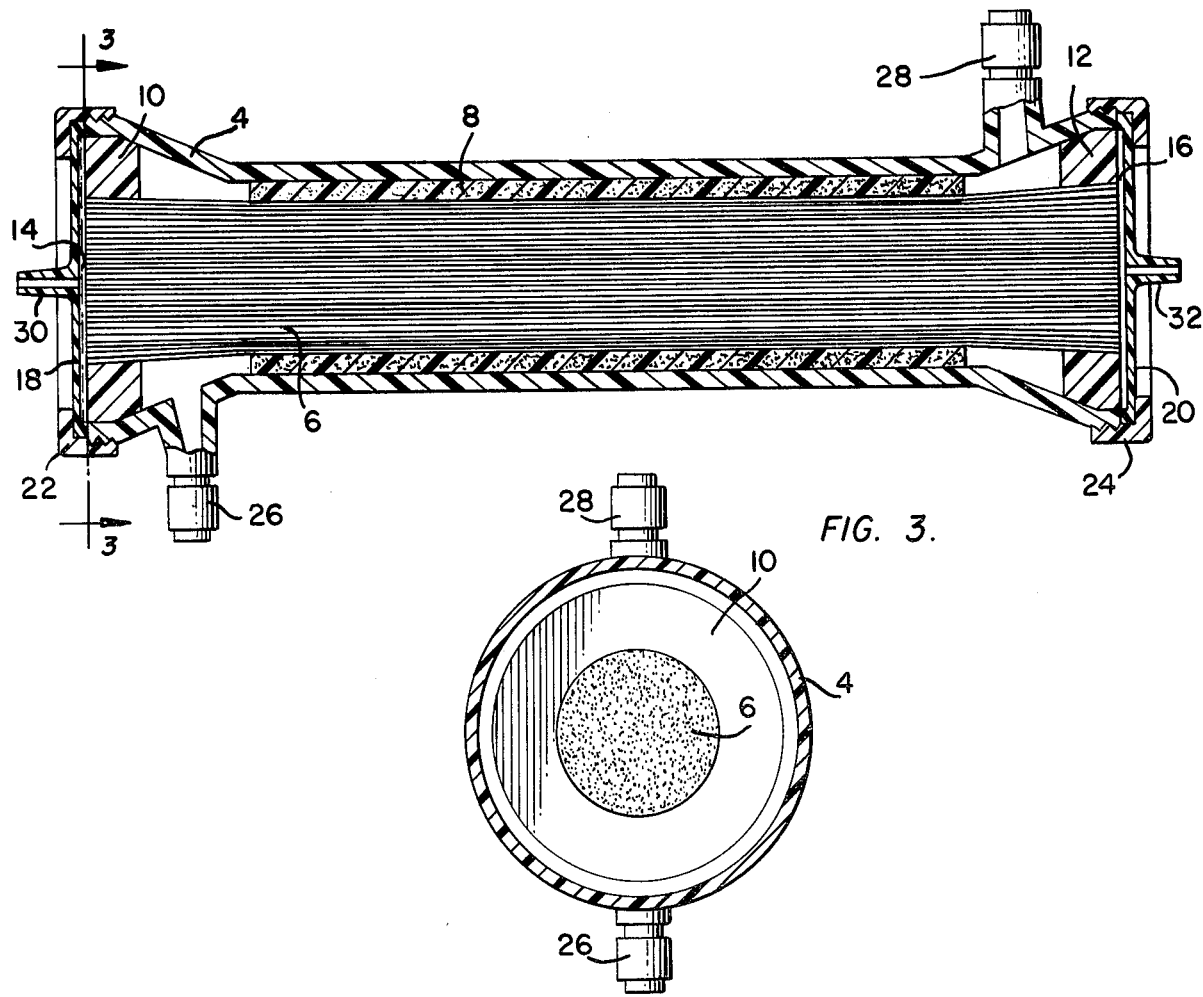
FIG. 2.
FIG. 3.

STERILIZATION OF DIALYZER

BACKGROUND OF THE INVENTION

The present invention relates to a method for sterilizating a dialyzer, especially a dialyzer for clinical use.

Recent progress in the art relating to artificial internal organs has been remarkable. Above all, various artificial kidneys have been created, miniaturized, improved in safety and made easy to use. Further, a dialyzer for use with the living body, based on the same principles, has been strenuously studied for use as an artificial liver or for utilization as an ultrafiltration apparatus for use with the living body.

In the field relating to sterilization of dialyzers for the living body, namely, artificial kidneys which have heretofore been used in actual practice, various methods have been used. These include the gaseous sterilization method, which uses ethylene oxide gas, and an alternative method which involves filling with an aqueous solution of formalin.

In the ethylene oxide gas method, a remarkable reduction of the performance of the dialyzer is sometimes encountered as a result of the sterilization procedure. Further, a very substantial preparation procedure is required, including washing for removal of poisonous residual gas, and of harmful substances produced by reaction with the sterilizing gas. Further, in the case of a hollow filament dialyzer which is one of the most advanced forms of dialyzer, it is necessary completely to replace the contents of the interiors of about 10,000 hollow filaments, each having an inner diameter of a few hundred microns, with physiological saline at the time of use. Indeed, if air or bubbles remain, circulation of blood may become obstructed, and this may become a cause of thrombosis. Further, the performance of a dialyzer is downgraded as a result of the sterilization procedure, and the valuable characteristics of the hollow filament dialyzer are at least partially lost. Further, the procedure of completely replacing the contents of the interiors of hollow filaments with physiological saline requires a remarkable amount of trouble and time.

The method of filling with an aqueous solution of formalin is said to have adequate sterilization effectiveness when a formalin solution of more than a certain concentration is used. However, the toxicity of the residual formalin at the time of use presents a safety problem. In order to completely wash and remove the formalin, washing for a very considerable time is necessary. Even then the problem remains regarding unfavorable side effects, which may be caused by even a trace of residual formalin. This process also presents another problem—that of disposal of the applied formalin solution.

On the other hand, sterilization by radial rays using gamma-rays or electron rays exerts a destructive influence on ordinary materials. Therefore, irradiation is limited to specific uses on materials having good resistance to the effects of radial rays. However, it is known that cellulose, polymethyl methacrylate and polyacrylonitrile, which are preferred for use as a semipermeable membranes and enhance the performance of an artificial kidney or a dialyzer for use with a living body, have poor resistance to the effects of such irradiation. Thus, they suffer great physical and chemical damage and their performance, extraction capability and strength are damaged.

Sterilization by application of radial rays can be practiced on a product that is completely wrapped and packaged. Accordingly, if the foregoing drawbacks were to be overcome, the use of radial rays would provide a very excellent sterilization method. The possibility of recontamination after sterilization would be eliminated and there would be no unfavorable side effects due to residual antibacterial agents.

One of the main reasons why sterilization by application of radial rays has not been effective in conjunction with most advanced hollow filament dialyzers resides in the toxicity of the extracts created by irradiation and in the destructive influence of radial rays, such as interference with the performance of the dialysis membranes. We have previously conducted studies of the problem of sterilization use of radial rays. We have found that such a dialyzer may be irradiated with radial rays while the dialyzer is filled or substantially filled with an aseptic inorganic aqueous solution which is harmless to a living body (such as aseptic water or physiological saline). Surprisingly, with such treatment it is possible to avoid significant destruction of the dialysis membranes. By so doing, it is possible to irradiate the dialyzer with an amount of radial rays which is sufficient to sterilize the dialyzer without producing undesirable extracts and without significant deterioration of the performance characteristics of the dialyzer.

It has further surprisingly been found, however, that it is necessary to reduce the number of contaminating bacteria to as small a value as possible before undertaking such a sterilization procedure. When the dialyzer is in a dry condition, or in a similar condition containing only a plasticizer such as glycerin for the semipermeable membrane, the dialyzer must be manufactured as aseptically as is possible. It is then possible to limit or prevent multiplication of bacteria to such a degree that they multiply to an almost negligible extent prior to commencement of the sterilization procedure. This serves to prevent the creation of pyrogens subsequent to the sterilization treatment.

When the dialyzer is completely or substantially completely filled with water or an ordinary aqueous solution bacteria usually multiply prior to sterilization treatment. It is nevertheless possible subsequently to sterilize the bacteria completely. However, if pyrogens are present in the residual killed bacteria, the patient is subject to the complications of chill and of fever after using such dialyzer.

An object of the present invention is to eliminate such disadvantages and to provide an excellent sterilization method for a dialyzer for use by a living person, with increased safety. Another object is to provide for reducing labor for preparing for dialysis.

Other objects of the present invention, including the simplicity and economy of the same and the ease with which it may be applied to existing dialysis equipment, will become apparent hereinafter.

In accordance with this invention, wherein the dialyzer has a semipermeable membrane, the dialyzer is subjected to the steps of:

(a) saturating the semipermeable membrane with a liquid containing an antibacterial agent; and (b) irradiating the dialyzer with radiation rays sufficient to kill remaining microorganisms in the presence of the antibacterial agent.

In accordance with the present invention the dialyzer is washed after manufacture and is impregnated with aseptic water or physiological saline or a similar aqueous solution and an antibacterial agent. For example, the solution may be of a salt containing a proper amount of a substance having a bacteriostatic or antibacterial action, such as hydrogen peroxide. The solution is applied in an amount in excess of the amount needed for saturation of the semipermeable membrane. After impregnation with the water or solution, the dialyzer is wrapped or packaged in that condition and is thereafter (or even after further packing) irradiated with radiation rays in a predetermined amount to thereby sterilize the same.

BRIEF DESCRIPTION OF THE DRAWINGS

FIG. 1 is a perspective view of a hollow filament dialyzer that may be advantageously sterilized in accordance with the invention;

FIG. 2 is a sectional view of the hollow filament dialyzer shown in FIG. 1, taken along the lines and arrows 2—2 of FIG. 1;

FIG. 3 is a sectional view of the hollow filament dialyzer shown in FIG. 1, taken along the lines and arrows 3—3 of FIG. 2.

DETAILED DESCRIPTION OF THE INVENTION

As referred to herein, the expression "dialyzer for a living body" is intended to include a wide variety of dialysis equipment intended for treatment of fluids in and from the human or animal body. It includes a disposable artificial kidney, and other dialyzers for similar clinical purposes. It also includes ultrafiltration apparatus which may be used for various purposes, as an artificial liver or artificial lung, for example. Further, a dialyzer treated according to the method of this invention may be incorporated into a part of a portable artificial kidney system or into an artificial liver system and used accordingly.

Although this invention has outstanding advantages as applied to a so-called hollow filament dialyzer as shown in the drawings, it is adaptable to dialyzers of many other types.

In the practice of this invention, it is necessary to wash the dialyzer with water which is as aseptic as reasonably possible, and a bacteriostatic or antibacterial agent in a proper amount is added. The wash water is preferably water purified by filtration, ion exchange, inverse osmosis and/or distillation.

Many different semipermeable membranes may be used in the dialyzers treated according to the method of the present invention. These include polymethyl methacrylates, cellulose, cellulose acetates, polycarbonates, polyacrylonitriles, modacrylic polymers and polyvinyl alcohols. Indeed, the present invention can be effectively applied to semipermeable membranes made up of other materials unless the resistance of the material to radial rays is especially inferior. The preferred molecular weights of these polymers are:

polymethyl metacrylates: 100,000—1,500,000
cellulose: 30,000—650,000
cellulose acetates: 30,000—650,000
polycarbonates: 30,000—500,000
polyacrylonitriles: 30,000—300,000
modacrylates: 30,000—300,000
polyvinyl alcohols: 40,000—200,000

Various hollow filament membrane shapes may be used in the practice of the present invention. However, a hollow tube membrane having an outer diameter of about 40-800 microns and a ratio of inner diameter to outer diameter of about 0.5-0.95 is often used.

The present invention may be applied to dialyzers of various forms. It is equally applicable to so-called disposal dialyzers having a structure including a large number of overlapping flat membranes, a so-called folded film dialyzer including a plurality of flat folded membranes, a coil dialyzer or a hollow filament dialyzer consisting of a bundle of hollow filaments. However, based upon our experience, it is best to apply the present invention to a hollow filament dialyzer of the type shown in the drawings with the dialysis liquid on one side (such as the outer surfaces of the filaments) and with the blood or other body fluid on the other side (such as on the inner surfaces of the hollow filaments.)

With reference to the Drawings, there is shown a hollow filament dialyzer 2 that is advantageously sterilized in accordance with the method disclosed herein. Dialyzer 2 comprises an elongated fluid-tight tubular casing 4 and a multiplicity of elongated hollow fibers 6 that are positioned within casing 4 in a relative close-packed relationship with the hollow fibers 6 extending in the direction of the casing's longitudinal axis. The group of hollow fibers is surrounded by a flexible sleeve member 8.

Each end of the tubular casing assembly 4 is closed by a potting agent defining fluid-tight sealing members 10, 12, respectively. The hollow fibers 6 extend substantially parallel to each other and through the sealing members 10, 12 with the open ends of the fibers 6 communicating with chambers 14, 16 that are formed between the sealing members and headers 18, 20 that are secured to the casing 4 in fluid-tight relation thereto by threaded coupling members 22, 24. The sealing members may comprise polyurethane consisting of (A) a prepolymer having isocyanate at the terminal thereof (B) a castor oil or derivative thereof. The prepolymer may consist of diisocynate and a castor oil or a derivative thereof.

As shown in FIG. 3, the spaces between the parallel filaments 6 are sealed by the sealing members and the open ends of the filaments extend through the sealing material and terminate along the endwise portions of the sealing members 10, 12, that are bordered by the chambers 14, 16, respectively.

The casing 4 is provided with dialysis liquid inlet 26 and permeate exit 28 that are disposed at opposed end portions of the casing. Headers 18, 20 include tapered openings 30, 32, that provide for entry and exit of the desired fluid feed, such as blood. As a material for the headers that form chambers for the introduction and discharge portion of blood, high density polyethylene may be preferably used. Polystyrene is preferably used as the casing for the dialyzer as a whole.

Dialysis liquid can be circulated about the outer surfaces of the hollow filament 6, while blood is passed through the interior of the hollow filaments via entry through inlet 30 and exit through port 32. Undesirable components of the blood permeate through the walls of the filaments and are washed out of the casing 4 through exit 28, while the thus purified blood exits at port 32.

It is important that the dialyzer, in practicing the present invention, shall include a semipermeable membrane containing moisture in excess of the saturated moisture content. The saturated moisture content as referred to herein is directed to the condition of the semipermeable membrane in which its pores are essentially completely filled with water or with an aqueous solution or suspension. The percentage of moisture in a saturated condition at the time of irradiation varies depending upon the nature of the material constituting the semipermeable membrane. The performance and characteristics of the semipermeable membrane often cannot be regulated uniformly. However, when the dialyzer is made ready for use, it is immersed in water sufficiently to bring about saturation. In this manner it is possible for substantially any of the appropriate membrane materials to achieve moisture contents equivalent to saturation of such semipermeable membranes, the degree of saturation varying according to the particular characteristics of the respective semipermeable membranes. To provide a semipermeable membrane which contains an excess of moisture, it is quite easy simply to fill the interior of a dialyzer completely or substantially completely with an aqueous solution or the like. If, for example, after the interior of a dialyzer has been filled with an aqueous solution, and after the solution has been subsequently discharged from the dialysis liquid side and/or from the blood side, the water still adhering to the surfaces of the hollow filaments is sufficient to maintain the desired water-containing or gelatinous condition of the surfaces of the filaments. Results are satisfactory so long as the hollow filaments are more than saturated, as though still immersed in water. However, it is preferred to fill the interiors of the hollow filaments with the aqueous solution, as opposed to filling the exterior space, because this does not require removal of bubbles from the hollow filaments.

Regarding the nature of the water used for filling the dialyzer, it should be as aseptic as is reasonably possible. The aqueous solution may be obtained by adding a proper amount of a bacteriostatic or antibacterial agent to the water or to an aqueous solution of a salt of an inorganic ion generally existing in the living body. Common salt is an example.

It is desirable to use a preservative of the type normally used in medicines, for the bacteriostatic or antibacterial agent. Examples include surface active agents such as paraoxybenzoic acid esters, phenols, chlorobutanols and benzalkonium chloride; sulfites; antibacterial agents of the chlorine series such as sodium hypochlorite, formalin or hydrogen peroxide aqueous solution. The kind and concentration of the bacteriostatic or antibacterial agent should be selected depending upon the properties and number of living bacteria to be encountered in manufacture. However, we prefer hydrogen peroxide water.

It has been found that microorganisms produced in the aseptic step grow and multiply under poor nutritional conditions when the dialyzer is filled with pure water or with an aqueous solution of an inorganic salt. They are very special bacteria, and it has been found that their multiplication is effectively prevented in the presence of a hydrogen peroxide aqueous solution having an $H_2O_2$ content of at least about 4 ppm, preferably about 5-200 ppm. Such multiplication can also be prevented by irradiation with radial rays in the presence of hydrogen peroxide. The hydrogen peroxide is almost completely decomposed. After irradiation the amount of hydrogen peroxide which remains is about equivalent to that produced when pure water is irradiated. Accordingly, the amount of hydrogen peroxide remaining in a dialyzer, after it has been sterilized by irradiation with radial rays, is very small. It can be quickly washed away by use of a small mount of physiological saline solution.

The application concentration of hydrogen peroxide for use in the practice of this invention varies from case to case, depending upon the kind and properties of microorganisms remaining in the dialyzer. However, the practical lower limit is about 5 ppm. There is no theoretical upper limit, from the point of view of the bacteriostatic or antibacterial effect, and excess concentration does not present any problem. However, in order as much as possible to limit the amount of hydrogen peroxide remaining after irradiation and to minimize the influence of the remaining hydrogen peroxide, a desirable upper limit is about 1000-2000 ppm. Even if an aqueous hydrogen peroxide solution of higher concentration is used, it may further prevent multiplication of bacteria before sterilization which is the direct effect of the present invention, but it does not diminish the effectiveness of the sterilization effect. Further, it is possible, depending upon the properties of the bacteria, to provide a greater effect by adding a substance other than hydrogen perioxide.

A dialyzer, wholly or substantially filled with an aqueous solution containing a bacteriostatic or antibacterial substance to be sterilized by irradiation with radial rays, should be irradiated with radial rays and sterilized after being packed or further wrapped with a material which is resistant to irradiation with radial rays, for example, polyethylene.

The amount of the irradiating of radial rays is determined by taking into account the number of contaminating bacteria, and their kind and their properties before sterilization. However, when the dialyzer is manufactured with sufficient care to prevent contamination by bacteria, a dosage of at least about 2 Mrad, preferably about 2.0-5.0 Mrad, and especially preferably about 2.0-3.0 Mrad has been found to be sufficient.

Usable radial rays include gamma-rays and high-speed electron rays. Suitable rays which are used relatively often are gamma-rays of cobalt 60.

If a dialyzer to which the present invention is applicable is manufactured of a selected material which is resistant to harm by radial rays so that the function and safety of the dialyzer (such as the toxicity of the extracts) will not be harmed, the dialyzer is not limited at all with respect to the structure, type or kind of material used in the semipermeable membrane.

After assembling a dialyzer, it is desirable to carry out the sterilization treatment as soon as possible, to prevent undue multiplication of contaminating bacteria before sterilization. In the case of a dialyzer filled with water or an aqueous solution, the sterilization treatment should be carried out within a very short period of time. However, according to the present invention, even if a dialyzer is allowed to stand for a few days after having been filled with water or an aqueous solution of an inorganic salt, very few if any living bacteria are detected within the dialyzer. Accordingly, even if the so-sterilized dialyzer is tested for pyrogenic properties, there is no problem in this respect. The concentration of hydrogen peroxide in the water, after sterilization by irradiation with radiation rays, becomes less than a few ppm, which is on the same level as the concentration of the residual hydrogen peroxide produced when radiation rays are projected into pure water, and this residue can be washed away very easily.

The present invention accordingly prevents multiplication of bacteria before sterilization by irradiating with radiation rays in a dialyzer filled or impregnated with pure water, or with an aqueous solution of an inorganic salt such as physiological saline, for example.

Hereinafter, the present invention will be explained by reference to specific examples which are not intended to define or to limit the scope of the invention, which is defined in the appended claims.

EXAMPLE 1

A dialyzer made up of hollow filaments of polymethyl methacrylate was assembled and manufactured. It was washed well with water sterilized as much as possible. Thereafter, the dialyzer was filled with physiological saline and allowed to stand at 30° C. for 10 days. Multiplication of bacteria in the physiological saline inside the dialyzer was observed. These bacteria were separated and cultivated in a standard agar culture medium, and were maintained suspended in a sterilized physiological saline solution until the number of the living bacteria became $10^5$/ml. The resulting suspension was divided and poured into 8 test tubes, to which tubes hydrogen peroxide solutions of 8 different concentrations were added. These concentration levels are shown in Table 1. The numbers of living bacteria after one day and after 10 days were measured by use of the membrane filter method. A similarly prepared suspension of bacteria in physiological saline containing added hydrogen peroxide was irradiated with $2.5 \times 10^6$ R of gamma-ray and the concentrations of hydrogen peroxide present before and after irradiation were measured. In each case, a suspension of the bacteria in physiological saline not containing hydrogen peroxide was used as a comparative example.

As is shown in Table 1, when at least 4 ppm of hydrogen peroxide were added, a bacteriostatic or antibacterial effect was observed. When at least 8 ppm of hydrogen peroxide were added, living bacteria were not found. Accordingly, to contaminating bacteria resulting from the manufacturing step of this dialyzer, the addition of at least 4 ppm of hydrogen peroxide was considered sufficient. However, depending upon the nature of the manufacturing procedures, the possibility exists that bacteria having strong resistances or tolerances may be generated; therefore, upon actually using hydrogen peroxide in a given case, the existing conditions should be considered and taken into account in determining the amount of $H_2O_2$ to add.

The concentration of hydrogen peroxide after irradiating with use of $2.5 \times 10^6$ R of gamma-rays decreased sharply. When the amount of hydrogen peroxide added was not above 200 ppm, the amount of hydrogen peroxide was about the same as the amount of hydrogen peroxide produced by irradiating with gamma-rays a physiological saline solution containing no hydrogen peroxide. They were present in such a concentration and amount that they were easily removed by washing.

Table 1

| Run No. | Concentration of $H_2O_2$ (ppm) | Number of living bacteria (bacteria/ml)[*1] | | Concentration of remaining $H_2O_2$ (ppm) | |
| --- | --- | --- | --- | --- | --- |
| | | After 1 day | After 10 days | Before irradiation | After irradiation [*2] |
| 1 | 1 | $1.8 \times 10^5$ | $1.9 \times 10^4$ | 0.5 | 3.4 |
| 2 | 2 | $3.0 \times 10^3$ | $3.5 \times 10^4$ | 0.9 | 1.4 |
| 3 | 4 | $7.8 \times 10^2$ | 0 | 1.9 | 3.6 |
| 4 | 8 | 0 | 0 | 1.9 | 2.7 |
| 5 | 40 | 0 | 0 | 19 | 2.4 |
| 6 | 200 | 0 | 0 | 98 | 8.0 |
| 7 | 400 | 0 | 0 | 217 | 107 |
| 8 | 2,000 | 0 | 0 | 1,082 | 534 |
| Comparative Example | 0 | $1.1 \times 10^5$ | $1.7 \times 10^6$ | 0 | 3.6 |

[*1] preserved at 30° C.
[*2] measured one week after irradiation

EXAMPLE 2

Two dialyzers made up of hollow filaments of a polymethyl methacrylate polymer were assembled and washed thoroughly with water which had been sterilized as much as reasonably possible. Thereafter, the interiors of these dialyzers were filled with a physiological saline solution containing 50 ppm of hydrogen peroxide, and were allowed to stand at 30° C. for 10 days. As comparative examples, four dialyzers were filled in a similar manner but with physiological saline not containing hydrogen peroxide. Two of these were allowed to stand at 30° C. for 1 day and the remaining two were allowed to stand at 30° C. for 10 days. After the designated time lapse, the liquids which had filled in the blood circuits of the respective dialyzers were collected and measured to determine the number of living bacteria present, using the membrane filter method. The results are shown in Table 2.

From the dialyzers filled with 50 ppm of hydrogen peroxide, no living bacteria were detected and satisfactory control of contaminating bacteria in this manufacturing step was achieved under this condition.

In contrast thereto, in the comparative examples, the number of living bacteria one day after the filling was 4-10/ml, and jumped to $4.5-9.4 \times 10^5$/ml after being allowed to stand for 10 days. Even when these bacteria were sterilized with radial rays, formation of pyrogens due to killed bacteria could not be prevented.

When $2.5 \times 10^6$ R of gamma-rays were irradiated into the dialyzers of this example to sterilize the same and thereafter tests for pyrogenic properties, acute toxicity, and hemolysis were carried out based on standard test methods for an artificial kidney. The results were adjudicated negative in all of these respects. Performance tests were carried out, and no reduction of dialyzing performance was recognized.

Table 2

| | Number of living bacteria (bacteria/ml)* | |
| --- | --- | --- |
| | After 1 day | After 10 days |
| Example (1) | — | 0 |
| (2) | — | 0 |
| Comparative Example (1) | 4 | $4.5 \times 10^5$ |
| (2) | 10 | $9.4 \times 10^5$ |

*Preserved at 30° C.

EXAMPLE 3

Three dialyzers each made up of hollow filaments of polymethyl methacrylate were assembled and washed. Thereafter, they were filled with physiological saline containing 8, 50 and 200 ppm of hydrogen peroxide, respectively, and irradiated with $2.5 \times 10^6$ R of gamma-rays. Thereafter, circuits on the dialysis liquid side and the blood side of each of these three dialyzers were washed with physiological saline flowing at a rate of 50 ml/min, and the concentration of hydrogen peroxide in the wash liquid was measured. As a result, in the dialyzer filled with physiological saline containing 8 ppm of hydrogen peroxide, after washing for 2 minutes, hydrogen peroxide was not detected. In the dialyzers filled with physiological saline containing 50 ppm and 200 ppm of hydrogen peroxide, respectively, hydrogen peroxide was not detected in either after 10 minutes. After washing, biological tests were carried out the same as in Example 2. The results were negative in all respects and no change of performance was recognized.

The washability of a commercially available hollow filament dialyzer filled with formalin water was investigated. When the dialyzer was washed with physiological saline at a flow rate of 500 ml/min on the dialysis liquid side and 200 ml/min on the blood side for 30–60 minutes, a clinitest was conducted and formalin was not determined to be present. However, further detailed examination revealed that 1–10 ppm of formalin remained.

EXAMPLE 4

Four dialyzers, each made up of hollow cellulosic filaments were washed with aseptic water. Thereafter each of one pair was filled with purified water containing 0 ppm and each of the other pair was filled with 30 ppm of hydrogen peroxide solution. Those with hydrogen peroxide solution were irradiated with $2.5 \times 10^6$ R of gamma-rays of cobalt 60 to effect sterilization. After filling the dialyzers with hydrogen peroxide solution until they were irradiated with gamma-rays, these dialyzers were allowed to stand at room temperature for 7 days.

On the other hand, the remaining two dialyzers washed with water and filled with pure water and hydrogen peroxide solution, at the same time, were tested to determine the number of contaminating bacteria, using the membrane filter method, before sterilization after 7 days. With reference to the two sterilized dialyzers, biological tests were carried out the same as in Example 3, and the filled liquid on the dialysis liquid side and that on the blood side were extracted before washing and subjected to endotoxin texts. The number of contaminating bacteria before sterilization was $4.0 \times 10^5$ in the case of the dialyzer filled with purified water containing 0 ppm of hydrogen peroxide water, but it was 0 in the case of the dialyzer filled with purified water containing 30 ppm of hydrogen peroxide solution.

The results of the biological tests of the sterilized dialyzers were all negative. However, the endotoxin test of the filled liquid on the dialysis liquid side of the dialyzer filled with purified water containing 0 ppm of hydrogen peroxide water showed a positive result. Namely, depending upon the sanitary control conditions in the case of the dialyzer filled with 0 ppm of hydrogen peroxide solution, this dialyzer showed the possibility of generating pyrogenic side effects.

EXAMPLE 5

Two dialyzers made up of hollow filaments of the polymethyl methacrylate series were washed with aseptic water. Thereafter they were filled with two kinds of purified water containing 0 ppm and 10 ppm of formalin, respectively. After 10 days, gamma-rays were irradiated into both of these two dialyzers. The number of contaminating bacteria before sterilization was determined and biological tests were carried out the same as in Example 4.

In the case of the dialyzer filled with purified water containing 0 ppm of formalin, the number of living bacteria before sterilization was $3.7 \times 10^5$, whereas said number was 1 in the case of the dialyzer filled with purified water containing 10 ppm of formalin.

The results of the biological tests carried out on the respective dialyzers, after they had been irradiated with gamma-rays and sterilized, were all negative. However, the endotoxin test of the filled liquid only on the dialysis liquid side in the case of the dialyzer filled with purified water containing 0 ppm of formalin showed a positive result.

In the process of washing the sterilized dialyzer with physiological saline, when the concentration of formalin was examined, use of 1 liter of physiological saline resulted in detection of no formalin, after completion of the washing.

It will be apparent, as explained above, that while the present invention is effectively applicable to sterilization of medical instruments and objects other than a dialyzer for a living body, and that they may be sterilized in a similar way or with the use of similar principles, highly surprising and effective results are obtained in the sterilization of porous semipermeable membranes.

Although reference has been made herein to aqueous solutions of antibacterial agents, such as solutions of hydrogen peroxide for example, the invention is effective without regard to the technical distinction between true solutions and suspensions or the like, so long as the surface of the object being sterilized is thoroughly wetted with an excess of a substantially uniform mixture of the liquid and the antibacterial agent.

Although this invention has been described with reference to specific types of dialysis membranes, irradiation rays and antibacterial agents, it will be appreciated that other membranes, rays and agents may be substituted, provided they function in combination with one another in substantially the manner heretofore described in this specification. Further, it will be evident that equivalent elements may be substituted for those specifically described, that certain features may be used independently of other features, and that sequences of steps may be reversed, provided the membrane be saturated with the aqueous antibacterial agent and the irradiation take place in the presence of the aqueous antibacterial agent in accordance with the invention as defined in the appended claims.

What is claimed is:

1. A wet state sterilization method for a semipermeable membrane of a dialyzer the steps which comprise:
   a. saturating a semipermeable membrane of a dialyzer with an antibacterial agent suspended in a liquid; and
   b. irradiating said saturated membrane with microbiocidal radiation rays in the presence of said agent, said rays being applied in an amount to kill substantially all remaining microorganisms.

2. A method according to claim 1, wherein said dialyzer is an artificial kidney.

3. A method according to claim 1, wherein said semipermeable membrane is a hollow filament.

4. A method according to claim 1, wherein said liquid is water and said antibacterial agent is hydrogen peroxide.

5. A method according to claim 1, wherein said semipermeable membrane comprises polymethyl methacrylate.

6. A method according to claim 1, wherein said semipermeable membrane comprises cellulose.

7. A method according to claim 1, wherein said semipermeable membrane comprises polyacrylonitrile.

8. A method according to claim 1, wherein said semipermeable membrane comprises polycarbonate.

9. A method according to claim 1, wherein the amount of irradiated radiation rays is at least 2 Mrad.

10. A method according to claim 1, wherein said radiation rays are gamma-rays.

11. A method according to claim 1, wherein the amount of antibacterial agent in said aqueous solution is at least 4 ppm.

12. A method according to claim 1, wherein said radiation rays are electron rays.

13. A wet state sterilization method for a hollow filament semipermeable membrane, of an artificial kidney comprising:
   a. saturating a hollow filament semipermeable membrane of an artificial kidney in an aqueous solution containing hydrogen peroxide; and
   b. subjecting said saturated semipermeable membrane to irradiation with gamma-rays in the presence of said hydrogen peroxide.

14. A method according to claim 13, wherein the amount of hydrogen peroxide in said aqueous solution is at least 4 ppm.

15. A method according to claim 13, wherein said semipermeable membrane comprises polymethyl methacrylate.

16. A method according to claim 13, wherein said semipermeable membrane comprises cellulose.

17. A method according to claim 13, wherein said semipermeable membrane comprises polyacrylonitrile.

18. A method according to claim 13, wherein said semipermeable membrane comprises polycarbonate.

19. A method according to claim 13, wherein the amount of irradiated gamma-rays is at least 2 Mrad.

* * * * *